United States Patent [19]

Melvin et al.

[11] Patent Number: 5,109,843
[45] Date of Patent: May 5, 1992

[54] EXTRA TO-INTRACORPOREAL POWER SUPPLY

[75] Inventors: David B. Melvin; David M. Brooks, both of Cincinnati, Ohio

[73] Assignee: University of Cincinnati, Cincinnati, Ohio

[21] Appl. No.: 621,054

[22] Filed: Nov. 30, 1990

[51] Int. Cl.$^5$ .............................................. A61N 1/00
[52] U.S. Cl. ........................... 128/419 R; 128/419 PS; 623/3
[58] Field of Search ......... 128/419 R, 419 PS, 419 B, 128/897-899, DIG. 25, 780; 623/3; 600/13-15

[56] References Cited

U.S. PATENT DOCUMENTS

| | | | |
|---|---|---|---|
| 3,731,669 | 5/1973 | Fitzgerald | 128/899 |
| 4,056,097 | 11/1977 | Maass | 600/13 |
| 4,143,661 | 3/1979 | LaForge et al. | 128/419 PS |
| 4,432,363 | 2/1984 | Kakegawa | 128/419 PS |
| 4,800,901 | 1/1989 | Rosenberg | 128/899 |
| 4,895,150 | 1/1990 | Isaacson et al. | 128/419 R |

FOREIGN PATENT DOCUMENTS 0602195 4/1978 U.S.S.R. .................. 128/419 PS

OTHER PUBLICATIONS

J. C. Schuder et al.: Energy Transfer Into a Closed Chest by Means of Stationary Coupling Coils and a Portable High-Power Oscillator, Transactions of the Assoc. for the Society of Artificial Internal Organs, 7, 327-329 (1961).
C. Sherman et al.: Energy Transmission Across Intact Skin for Powering Artificial Internal Organs, Trans. Am. Soc. Artif. Inter. Organs (1981), pp. 137-139, vol. 27.
J. D. Hardy: Body Temperature Regulation, Medical Physiology, 14th Edition, p. 1419.
D. H. LaForge et al.: The Belt Skin Transformer for Energy Transmission to Implanted Circulatory Support Devices, Art. Org., Proc. Int. Symp. on Artif. Organs, Biomedical Eng. & Transplantation, Ed. J. D. Andrade, VCH Publications, pp. 95-107 (1987).
K. A. Dasse et al.: Biological Consequences of Chronic Transcutaneous Energy Transmission, Progress in Artificial Organs, 1127-1130 (1985).
C. F. Andren et al.: The Skin Tunnel Transformer: A New System That Permits Both High Efficiency Transfer of Power and Telemetry of Data Through the Intact Skin, IEEE Transactions on Bio-Medical Engineering, vol. BME-15, No. 4, (10/68).
G. H. Myers et al.: A Transcutaneous Power Transformer, vol. XIV, Trans. Amer. Soc. Artif. Int. Organs, pp. 210-214 (1968).
M. Lipkin et al.: Measurement of Some Thermal Properties of Human Tissues, Journal of Applied Physiology, 7, 212-217 (1954).
Rawson, R. O. et al.: Visceral Tissue Vascularization: An Adaptive Response to High Temperature, Science, 158, 1203-1204 (1967).
Newgard, P. et al., "Skin Transformer and Power Conditioning Components," Proceedings of the First Artificial Heart Program Conference, pp. 927-936 (Jun. 1969).
Guyton, A. C., "Body Temperature, Regulation and Fever," Textbook of Medical Physiology, 8th Edition, p. 797 (1991).
Grover, F. W., Inductance Calculations: Working Formulas and Tables, New York: Dover (1973), pp. 123-137 and pp. 150-162.

Primary Examiner—William E. Kamm
Assistant Examiner—Kennedy J. Schaetzle
Attorney, Agent, or Firm—Wood, Herron & Evans

[57] ABSTRACT

A method of providing extracorporeal to intracorporeal power transfer in a patient employs a cylindrical primary coil inserted into a segment of small intestine which has been separated and closed at one end. The open end is attached to the abdominal wall providing an opening to the exterior of the body. A secondary coil is formed by wrapping a wire around the serosa of the segmented small intestine. This is in effect a transformer which will transfer energy from the primary coil to the secondary coil. The vascularization of the segment provides for rapid and efficient heat dissipation. This device can be used to power heart assist devices and artificial hearts. Since it is located in an internal pouch, proper location of the primary coil is ensured.

7 Claims, 1 Drawing Sheet

EXTRA TO-INTRACORPOREAL POWER SUPPLY

BACKGROUND OF THE INVENTION

There are a number of internal power consuming prosthetic devices now employed or contemplated for implantation in the human body. A common problem with all of these devices is providing an effective, safe power supply. Smaller devices such as pacemakers can use replaceable batteries. The necessity of surgically replacing batteries periodically is not a significant problem. With respect to devices requiring more power than the pacemaker battery supplied power is inadequate. Devices such as artificial hearts require up to 20 watts of continuous power. A battery designed to provide such power for 60 days would weigh at least 20 kilograms. Nuclear power supplies are also inappropriate since the shielding requirements would make these unsuitable. Further, if the shielding failed, the results could be catastrophic.

All devices used in humans for mechanical circulatory assistance have, therefore, required a permanent opening in the skin for energy transfer. These include pneumatic conduits for balloon pumps, the Jarvik total artificial heart and the Thermo Medical Systems assist device, blood conduits for the Thoratec (Pierce-Donachy) and Abiomed sacular pumps, an electrical cable for the Novacor solenoid pump and a spinning torque cable for the Nimbus Hemo pump intravascular turbine. Whereas these have occasionally been used for extended periods without infection (over two years in one Jarvik patient and over ten months in a current Novacor recipient), clinical and experimental observations indicate that such an integumental break presents a continuing risk of infection.

Principally for this reason, none of these devices except the Jarvik have been seriously proposed for long term circulatory support. All the others have been promoted as strictly temporary aid for use during expected cardiac recovery or during the waiting period for a transplant donor. Infections have been minimal for these short periods.

Electrical induction has long been entertained as a means of delivering power from extracorporeal source across intact integument. In 1961, a transformer operating with radio frequency alternating current from an external to a subcutaneous coil was reported by Schuder, Stephenson and Townsend. It was reasoned that a coil within a coil configuration could be more efficient and a tube pedicled skin flap was utilized. Within this tube of skin (shaped like a suitcase handle and attached to the chest wall at either end) lay a secondary coil while the primary coil with an iron core (allowing a lower frequency current to be used), surrounded it. Efficiencies of 97% (57 watts, 20 kHz) were reported.

Two groups of investigators have pursued these concepts for the past decade and have been developing inductive energy transmission systems seriously intended for powering of clinical circulatory assist devices. A belt skin transformer was developed by LaForge at Novacor which consists of a narrow single turn flexible secondary coil implanted in the subcutaneous tissue around the waist and a five turn extracorporeal primary coil worn in a belt. This has effectively transmitted 15 watts of continuous power at more than 75% efficiency in both in vitro models and experimental animal models. This system is intended to be coupled with a modified version of Novacor's current temporary solenoid operated intracorporeal left ventricular assist system to form a support system for long term use. Animals with the implanted device have survived for over two years with little difficulty reported.

An induction device has been developed by Thermedics, Inc. (now Thermo Medical Systems) which is situated in and on the anterior abdominal wall. The implanted secondary coil is made of 16 turns of braided copper wire wrapped around a dome-shaped polyurethane appliance within the abdominal subcutaneous tissue. The primary is a 3 turn coil in a ring that is worn surrounding the mound produced by the secondary appliance and secured by a belt. Transmission of 24 watts has been demonstrated. In efficiency studies in animals this has delivered 6 to 12 watts of usable power with a 3 watt loss (65%-70% efficiency). Most of the losses were demonstrated in external components and about 1 watt was lost in the transformer itself, presumably as heat. A clinical form of this device is to be used with an electric version of Thermo Medical System's current pneumatic left ventricular assist system.

These devices seem likely to offer a practical means for extra to intracorporeal energy transfer. Consideration of their use in patients, however, suggests some possible problems.

The only known prior use of a life supporting device that had to be maintained in the surface position was the radiofrequency induction coil used in pacemakers before introduction of satisfactory implantable batteries. These worked very well electrically (the very low power requirements of pacemakers needed a much less efficient inductor than assist devices) but there was a high fatality rate clinically due to inadvertent displacement by the patient.

Further, changes in electrical load of a pumping device or minor component failure in the activating circuit can potentially increase the heat produced in implanted secondary coils. Potential for dissipation of this heat without damage to surrounding tissue is limited by tissue blood supply. A serious burn of the tissue layer separating the primary and secondary coils could lead to device infection. Further, the discomfort and annoyance of a device that the patient can constantly feel in contact with his or her skin compounded by this psychological impact of knowing that that itch, tickle, or irritation is to be there for life is impossible to anticipate or calculate.

SUMMARY OF THE INVENTION

It is accordingly an object of the present invention to provide a new extra-to intracorporeal power transformer. More particularly, the present invention is premised on the realization that an isolated segment of small intestine can be closed at one end and at the opposite end attached to the surface of the skin providing an implanted pouch which can hold a primary coil. An intracorporeal secondary coil can be formed on the serosa of the intestinal segment.

The intestinal segment presents a thin layer of very well vascularized tissue with accessible intracorporeal and extracorporeal surfaces without the need for devascularizing dissection. It is naturally tubular making it suitable for an efficient transformer design (coil within a coil). This surgical procedure is similar to a surgical technique used for isolating a segment of small intestine connecting one end to the abdominal skin to use it as a conduit for urine after bladder removal.

The present invention provides for the use of a cylindrical coil within a coil transformer design which is particularly efficient. Further, if additional power is required, two such devices can be implanted at different locations to provide for greater power input. Such a system for extracorporeal to intracorporeal energy transfer is useful for any electrically operated power-consuming internal prosthetic device and particularly suitable for heart assist devices such as artificial hearts.

The objects and advantages of the present invention will be further appreciated in light of the following detailed descriptions and drawings in which:

DETAILED DESCRIPTION

An extra to intracorporeal power supply is basically an air core transformer whose primary coil is a cylindrical coil inserted into an ileal sac which is formed from a dissected portion of the small intestines and sewn to the abdominal wall leaving a cutaneous stoma.

The secondary winding is located within the body cavity surrounding the ileal sac. The secondary winding can then lead to an electrically powered prosthetic device within the body cavity.

Figure 1:
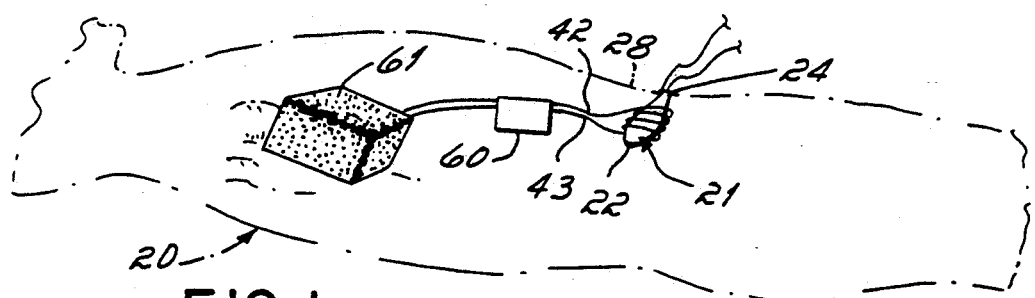
FIG. 1 is a diagrammatic view of a patient with the implanted device of the present invention.
Figures 2, 3:
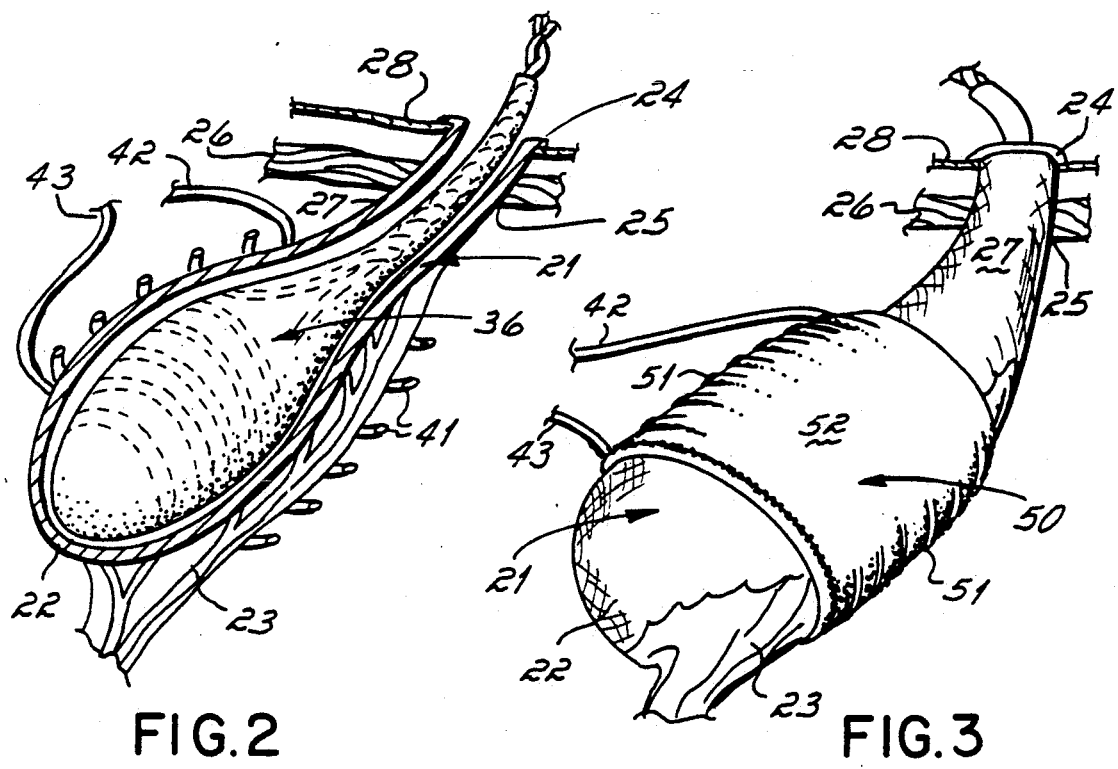
FIG. 2 is a diagrammatic view of an ileal sac incorporating the present invention partially in cross section.
FIG. 3 is a diagrammatic view of an alternate embodiment of a completed intestinal pouch with the secondary coil in place.

More particularly, as shown in FIG. 1, the patient 20 has an ileal sac 21 which includes a sutured or closed end 22 and a cutaneous stoma 24. As is shown in FIG. 2, the mesentery 23 remains attached to the ileal sac 21. Further, as more particularly shown in FIG. 2, the ileal sac includes a primary coil implant 36 which is located in the interior of the ileal sac 21. Surrounding the ileal sac 21 is the secondary coil 41.

The ileal sac 21 is formed from a section of the small intestine. A segment of the small intestine is selected and surgically isolated. The remaining bowel is then reconnected. This is the same procedure used in the formation of an ileal urinary diversion loop and as such, is a well known operative procedure. The length of the segment of small intestine will in large part be determined by the vasculature of the segment. Removal of the segment should not interrupt or intersect any blood flow from the mesentery to the selected segment. The selected segment with mesentery is then sutured shut at one end as indicated by 22 in FIG. 2. As shown in FIG. 2, the mesentery 23 remains attached to the formed ileal sac 21.

A cutaneous stoma 24 is then formed in the lower abdominal region. To accomplish this, a small slit 25 is formed through the muscle tissue 26 and the first end 27 of the ileal sac is passed through slit 25 and sewn to the skin 28 to form the cutaneous stoma.

The specific construction of the pouch is dependent on the relative diameters of the primary coil appliance and intestinal segment selected. It can be formed as a simple segment, a doubled or "J" type pouch or a quadrupled pouch similar to that used in a Koch ileostomy. If a doubled or quadrupled segment is employed, a single pouch is formed by well-known operative procedures.

The secondary coil 40 is formed by taking a selected length of wire and wrapping this around the serosa (outer wall of the segment). As shown in FIG. 2, this can be simply wrapped around the serosa and the mesentery. Optionally, a wire can be passed through the mesentery as it is wrapped around the segment with care taken to avoid perforating any blood vessels. The leads 42 and 43 of the secondary coil can then be directed to the internal circuitry and batteries 60 which would lead to the internal power consuming prosthetic device 61 which in this case is depicted as a total artificial heart.

In an alternate embodiment, as shown in FIG. 3, the secondary coil can be a preformed coil 50 having wire windings 51 encased in a silicone sleeve 52. Where a preformed sleeve is employed, the sleeve may be slipped over the segment before or after the cutaneous stoma is formed, depending on which end the mesentery may exit with the least compression and distortion. The secondary coil 50 is held in stable relationships to the intestinal segment by suturing.

Again, the general method of forming an ileal sac and cutaneous stoma is the same method employed in the formation of a ileal urinary diversion loop which is a well known surgical procedure.

Figure 4:
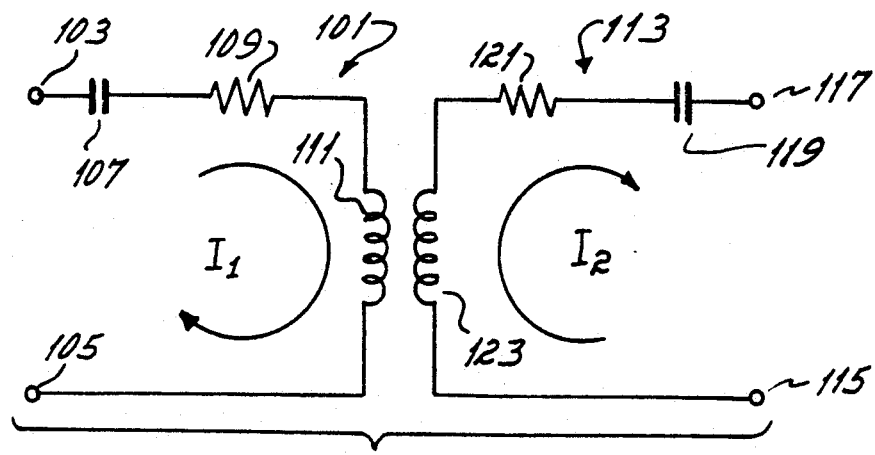
FIG. 4 is a diagrammatic depiction of the circuit used in the present invention.

A schematic diagram of the input circuit of an embodiment of the present invention is shown in FIG. 4. The primary loop 101 includes input terminals 103, 105 and a tuning capacitor 107. The resistance and the inductance of the winding are represented by resistor 109 and inductor 111, respectively. For purposes of illustration, a current is shown in the primary loop having a clockwise direction. The tuning capacitor 107 is selected for the input frequency range of the power supply as is well known within the art. The secondary loop 113 includes output terminals 115, 117 and a secondary tuning capacitor 119. The tuning capacitor 119 in the secondary loop 113 is used to compensate for the secondary inductive reactance. As explained below, the primary inductive reactance and reflected portion of secondary inductive reactance can also be compensated through the tuning of capacitor 107 alone eliminating the need for tuning capacitor 119. The resistance and the inductance of the secondary winding are represented by resistor 121 and inductor 123, respectively. The current in the secondary loop is illustrated as having a clockwise direction.

The mutual impedance, represented simply as $X_m$, between the loops can be determined from the two currents, the input voltage and the components in the primary loop by the equation $X_m = (V_1 - I_1(R_1 - X_{cl} + X_{11}))/I_2$. The mutual impedance may also be calculated using the component values in the secondary loop, the output voltage, and the two loop currents in accordance with the formula $X_m = -V_2[I_2(R_2 - X_{c2} + X_{12})]/I_1$. In both of these equations, the tuning capacitors in one or both of the loops have been adjusted to compensate for their respective inductive reactances. This compensation means the impedance of the tuning capacitor, which can be represented by a complex number, and the input circuit, which can also be represented by a complex number, have imaginary parts which are equal in magnitude but opposite in sign. Thus, the imaginary parts of the impedance values cancel one another out and the current is in phase with the voltage through the purely resistive components. At this point of resonance, i.e., where the tuning capacitor compensates for the imaginary component of the impedance, the input power is calculated by the formula $P_1 = V_1 \times I_1$ and the output power is calculated by the formula $P_2 = V_2 \times I_2$.

The primary coil is formed from braided copper Litz wire embedded in a low durometer medical grade silicone rubber tapered cylinder. Construction consists of handcrafting a ceramic model of identical size and shape as the intended primary appliance (generally 1.5 to 3 cm outside diameter and 5 to 10 cm long with an extended 1 cm "tail" for lead wires). A mold is made from this model using silicone rubber similar to that of the appliance itself. The wire is wrapped around a mandrel of a size that will produce an external coil diameter slightly smaller than the mold. A ribbon of uncured silicone rubber placed on the mandrel before wrapping is then cured to maintain coil integrity when the coil is removed from the mandrel.

The coil is removed from the mandrel, placed in the mold and filled with silicone rubber. Alternately the coil can be filled with ferrite powder before being coated with silicone to increase core inductance, to increase couples and improved efficiency. Generally about 36 gms of ferrite has been packed within the coil. Ferrox cube C385 brand ferrite is currently preferred. The mold includes a round first end and a tapered second end to form a primary coil implant as shown in FIG. 2. After curing, this is suitable for use as a primary coil implant for use in an ileal sac.

A secondary coil as shown in FIG. 3 is formed from silicone coated wire which is wrapped around the serosa with 1 to 2 turns per centimeter.

A preformed secondary coil, as shown in FIG. 3, is formed by again wrapping the wire around a mandrel and applying an uncured silicone rubber to the wire. The silicone is cured and the coil removed from the mandrel in a cylindrical appliance.

An appropriate length of wire should remain on either end of the coil to provide leads 42 and 43 for attachment to the prosthetic device.

To test the device, ileal implants were formed and implanted within canine test subjects. Physical characteristics of an intraluminal appliance that would fit the canine's small bowel segment with minimum distortion were outlined and a model built. The model had a curved (radius of curvature 15.25 centimeters) cylindrical (diameter 1.4 centimeters) configuration with one end rounded and the other tapered to a 0.6 centimeter diameter tube intended to extend through the cutaneous orifice and contain lead wires 42 and 43. It was cast of 40 durometer medical silicone rubber purchased from Dow Corning Corporation Medical Products MDX-4210 in molds of similar material made from an initial ceramic (polyform compound, Polyform Products, Inc.) handcrafted model.

The primary coils were built in a size and shape that would fit within this cylinder. Litz wire (copper, 400 strands of 40 gauge, braided 12 turns per inch, Kerrigan-Lewis, Inc. Chicago) was selected for its ability to conduct radiofrequency currents in the 100 kHz to 200 kHz range with minimal loss. Coils of this wire were mandrel wrapped in an appropriate diameter after applying a ribbon of uncured silicone rubber to one side and curing. These were removed, placed within the mold with the lead wires extending through a tube of similar material and the mold was injected with silicone rubber. The cylinders were cured.

Secondary coil configurations that would physically adapt to a segment of canine intestine with this primary coil appliance in its lumen was then determined. With the primary in place, a length of Litz wire was brought through an opening in the mesentery immediately adjacent the intestine carefully avoiding mesenteric vessels. After advancing half the length of the wire through the mesentery, each end of the wire was wound circumferentially towards one end of the cylinder on the serosal surface of a bowel using two corrugated silicone rubber guides. With each pass, the minimum traction needed to keep the wire in contact with the serosa was applied. Vessels were avoided with surgical telescopic magnification. After the ends were sutured to the mesentery, the secondary coil external diameter was measured. The thickness of the primary and secondary coil with the secondary thus loosely wound, was calculated.

Dual coil assemblies of similar geometry were constructed for bench testing, using appropriately sized latex tubes to separate and maintain position. A DC/AC invertor capable of providing up to 35 watts of power at frequencies of 100 kHz to 300 kHz from a 6 to 12 volt DC power supply was used to assess inductive characteristics of the coil assembly. Mutual reactance and inductance were measured using a series resonant circuit with a known capacitor, varying input frequency to resonance. Coupling was determined by open secondary transformer tests measuring output voltage and input current at resonant frequency.

In "bench" testing, efficiency of the entire system is 75%. Transformer efficiencies have been greater than 95%.

Thirteen canine implants as discussed above were conducted with thermisters (Clinical Swan-Ganz Catheters, Edwards Critical Care Division Baxter Health Care Corporation, Santa Anna, California) positioned between the turns of the secondary coil and situated remotely in the abdomen either in the pelvis or between the liver and the lateral abdominal wall. The animals were subjected for periods of 45 to 400 minutes of power transfer increasing stepwise to a peak from 2.5 to 15 watts. Excessive sustained (over 1° C.) temperature elevation did not occur in the absence of electrical malfunction (short circuits) or surgical problems (kinking of mesentery). These were avoided in the last several animals, demonstrating that the device can successfully provide power without causing excessive heat build up about the device. The vasculature of the bowel segment effectively removes significant amounts of heat generated during power transfer.

By employing the device of the present invention, an individual can use an electrically powered prosthetic device such as an artificial heart or a heart assist device. Since portable power supplies are available and economically, the patient can retain basic mobility.

This device is beneficial since the blood flow through the mesentery is relatively high and provides for dissipation of heat formed by such inductive devices. Further, since the intestinal wall lacks tactile sense, the device will not be as noticeable to the patient as would a device implanted in the skin.

Since the primary coil lies in a sac, inadvertent displacement is particularly unlikely and proper location is ensured.

This has been a description of the present invention together with the best mode of the invention currently known.

However, the invention should be defined only by the appended claims wherein we claim:

1. A method of implanting an extra to intracorporeal power supply within a body comprising:

attaching a vascularized intestinal segment to the abdominal wall said segment opened at the end attached to the abdominal wall and closed at the opposite end;

forming an internal secondary coil of wire around serosa of said intestinal segment with first and second ends of said wire remaining in said body;

inserting a primary coil through said open end into said intestinal segment whereby an alternating current passing through said primary coil causes an induction current in said secondary coil effective to power electrically operated prosthetic devices attached to said first and second ends.

2. The method claimed in claim 1 wherein said intestinal segment is a segment of small intestine.

3. The method claimed in claim 1 wherein said power supply has a power output of at least about 20 watts.

4. The method claimed in claim 1 wherein said primary coil comprises a wire wound cylinder.

5. The method claimed in claim 4 wherein said cylinder is silicone.

6. The method claimed in claim 1 wherein said secondary coil is a preformed coil and is slipped over the open end of said intestinal segment before it is attached to the abdominal wall.

7. A primary coil adapted for use as an extra to-intracorporeal energy transfer device comprising a cylindrical core having a rounded first end and a tapered second end separated by a cylindrical central section;

a wire having first and second ends said wire wrapped around said cylindrical central section;

said first and second ends passing from said cylindrical central section through said tapered second end.

* * * * *